United States Patent
Copa et al.

(10) Patent No.: US 8,636,756 B2
(45) Date of Patent: Jan. 28, 2014

(54) ANASTOMOSIS DEVICE AND SURGICAL TOOL ACTUATION MECHANISM CONFIGURATIONS

(75) Inventors: Vincent G. Copa, Minnetonka, MN (US); Kory P. Hamel, Bloomington, MN (US); Sidney F. Hauschild, St. Paul, MN (US)

(73) Assignee: AMS Research Corporation, Minnetonka, MN (US)

( * ) Notice: Subject to any disclaimer, the term of this patent is extended or adjusted under 35 U.S.C. 154(b) by 1834 days.

(21) Appl. No.: 11/356,556

(22) Filed: Feb. 17, 2006

(65) Prior Publication Data

US 2006/0206122 A1 Sep. 14, 2006

Related U.S. Application Data

(60) Provisional application No. 60/654,423, filed on Feb. 18, 2005.

(51) Int. Cl.
*A61B 17/08* (2006.01)
(52) U.S. Cl.
USPC ......................................................... 606/153
(58) Field of Classification Search
USPC ......... 606/106, 108, 127, 138, 139, 144, 153, 606/142; 623/1.23
See application file for complete search history.

(56) References Cited

U.S. PATENT DOCUMENTS

| | | |
|---|---|---|
| 4,701,162 A | 10/1987 | Rosenberg |
| 4,705,502 A | 11/1987 | Patel |
| 4,792,330 A | 12/1988 | Lazarus et al. |
| 4,813,934 A | 3/1989 | Engelson et al. |
| 4,848,367 A | 7/1989 | Avant et al. |
| 4,873,977 A | 10/1989 | Avant et al. |
| 4,909,785 A | 3/1990 | Burton et al. |
| 4,911,164 A | 3/1990 | Roth |
| 4,932,956 A | 6/1990 | Reddy et al. |

(Continued)

FOREIGN PATENT DOCUMENTS

| | | |
|---|---|---|
| WO | WO 92/04869 | 4/1992 |
| WO | WO 96/07447 | 3/1996 |

(Continued)

OTHER PUBLICATIONS

Igel et al., "Comparison of Techniques for Vesicourethral Anastomosis: Simple Direct Versus Modified Vest Traction Sutures," Urology, vol. XXXI, No. 6, pp. 474-477 (Jun. 1988).

(Continued)

*Primary Examiner* — Dianne Dornbusch
(74) *Attorney, Agent, or Firm* — Kagan Binder, PLLC (57) ABSTRACT

The tissue approximating structures for the anastomosis devices of the invention preferably include two sets of approximating structures or tines spaced from each other along the length of a catheter body that can be extended and retracted from the catheter body. Each of the sets of tissue approximating structures is preferably sequentially deployable in such a way that the surgeon can activate a first set of tines to engage a first tissue structure, verify that an adjacent second tissue structure is properly positioned relative to the first tissue structure, then activate a second set of tines to engage that adjacent second tissue structure. Each of the sets of tines is preferably controlled by a single actuation mechanism that is attached to the anastomosis device and is positioned outside the patient's body.

13 Claims, 5 Drawing Sheets

(56) References Cited

U.S. PATENT DOCUMENTS

| | | | |
|---|---|---|---|
| 5,047,039 A | 9/1991 | Avant et al. |
| 5,123,908 A | 6/1992 | Chen |
| 5,152,772 A | 10/1992 | Sewell, Jr. |
| 5,306,226 A | 4/1994 | Salama |
| 5,540,701 A | 7/1996 | Sharkey et al. |
| 5,545,171 A | 8/1996 | Sharkey et al. |
| 5,643,248 A * | 7/1997 | Yoon ................................ 606/1 |
| 5,653,690 A | 8/1997 | Booth et al. |
| 5,695,504 A | 12/1997 | Gifford, III et al. |
| 5,707,380 A | 1/1998 | Hinchliffe et al. |
| 5,833,698 A | 11/1998 | Hinchliffe et al. |
| 5,931,842 A | 8/1999 | Goldsteen et al. |
| 5,964,791 A | 10/1999 | Bolmsjö |
| 6,024,748 A | 2/2000 | Manzo et al. |
| 6,119,045 A | 9/2000 | Bolmsjö |
| 6,149,667 A | 11/2000 | Hovland et al. |
| 6,193,734 B1 | 2/2001 | Bolduc et al. |
| 6,238,368 B1 | 5/2001 | Devonec |
| 6,254,570 B1 | 7/2001 | Rutner et al. |
| 6,299,598 B1 | 10/2001 | Bander |
| 6,302,905 B1 | 10/2001 | Goldsteen et al. |
| 6,391,039 B1 | 5/2002 | Nicholas et al. |
| 6,416,545 B1 | 7/2002 | Mikus et al. |
| 6,440,146 B2 | 8/2002 | Nicholas et al. |
| 6,447,533 B1 | 9/2002 | Adams |
| 6,461,367 B1 | 10/2002 | Kirsch et al. |
| 6,485,496 B1 | 11/2002 | Suyker et al. |
| 6,494,908 B1 | 12/2002 | Huxel et al. |
| 6,520,974 B2 | 2/2003 | Tanner et al. |
| 6,530,932 B1 | 3/2003 | Swayze et al. |
| 6,562,024 B2 | 5/2003 | Alvarez de Toledo et al. |
| 6,565,579 B2 | 5/2003 | Kirsch et al. |
| 6,599,311 B1 | 7/2003 | Biggs et al. |
| 6,602,243 B2 | 8/2003 | Noda |
| 6,695,832 B2 | 2/2004 | Schon et al. |
| 6,702,825 B2 | 3/2004 | Frazier et al. |
| 6,719,709 B2 | 4/2004 | Whalen et al. |
| 6,719,749 B1 | 4/2004 | Schweikert et al. |
| 6,726,697 B2 | 4/2004 | Nicholas et al. |
| 6,740,098 B2 | 5/2004 | Abrams et al. |
| 6,746,456 B2 | 6/2004 | Xio |
| 6,746,472 B2 | 6/2004 | Frazier et al. |
| 6,821,283 B2 | 11/2004 | Barzell et al. |
| 2001/0049492 A1 | 12/2001 | Frazier et al. |
| 2002/0002363 A1 | 1/2002 | Urakawa et al. |
| 2002/0087176 A1 | 7/2002 | Greenhalgh |
| 2003/0069629 A1 | 4/2003 | Jadhav et al. |
| 2003/0208183 A1 | 11/2003 | Whalen et al. |
| 2003/0229364 A1 | 12/2003 | Seiba |
| 2004/0078047 A1 | 4/2004 | Nicholas et al. |
| 2004/0087995 A1 | 5/2004 | Copa et al. |
| 2005/0070938 A1 | 3/2005 | Copa et al. |
| 2005/0131431 A1 | 6/2005 | Copa et al. |
| 2005/0192602 A1 | 9/2005 | Manzo |
| 2005/0251155 A1 | 11/2005 | Orban, III |
| 2005/0288764 A1 | 12/2005 | Snow et al. |
| 2006/0200178 A1 | 9/2006 | Hamel |
| 2006/0206122 A1 | 9/2006 | Copa et al. |
| 2006/0264985 A1 | 11/2006 | Copa et al. |
| 2006/0276811 A1 | 12/2006 | Copa et al. |
| 2007/0219584 A1 | 9/2007 | Copa et al. |

FOREIGN PATENT DOCUMENTS

| | | | |
|---|---|---|---|
| WO | WO 99/16359 | 4/1999 | |
| WO | WO 99/21490 | 5/1999 | |
| WO | WO 99/21491 | 5/1999 | |
| WO | WO 99/58081 | 11/1999 | |
| WO | WO 00/78226 * | 12/2000 | ............... A61D 1/00 |
| WO | WO 04/000135 | 12/2003 | |
| WO | WO 04/000136 | 12/2003 | |
| WO | WO 04/000137 | 12/2003 | |
| WO | WO 04/000138 | 12/2003 | |
| WO | WO 2004/034913 | 4/2004 | |

OTHER PUBLICATIONS

Acconcia et al., "Sutureless" Vesicourethral Anastomosis in Radical Retropubic Prostatectomy, The American Journal of Urology Review, vol. 1, No. 2, pp. 93-96 (Mar./Apr. 2003).

* cited by examiner

Fig. 7

ANASTOMOSIS DEVICE AND SURGICAL TOOL ACTUATION MECHANISM CONFIGURATIONS

CLAIM FOR PRIORITY

The present application claims priority to U.S. provisional patent application No. 60/654,423, filed Feb. 18, 2005, and entitled "Anastomosis Device Actuation Mechanism Configurations." The identified provisional patent application is hereby incorporated by reference.

TECHNICAL FIELD

The present invention relates to devices used for performing anastomosis and other related surgical procedures, including urethral procedures that involve reconnecting urethra and bladder tissues after a radical prostatectomy, vesicourethral anastomosis, and end-to-end urethral anastomosis.

BACKGROUND OF THE INVENTION

Anastomosis procedures are required for connecting or re-connecting certain body tissues, e.g., as part of a surgical procedure. The tissues may be part of a body lumen such as a blood vessel, intestinal or other digestive system tissue, or tissues relating to the urinary system. As one example, in a radical prostatectomy, a surgeon removes all or most of a patient's prostate. Because the urethra travels through the prostate immediately before reaching the bladder, the upper part of the urethra is also removed with the surgery. The procedure leaves a severed urethral stump and a severed bladder neck. To restore proper urinary functions, the bladder and the urethra must be reconnected.

Conventionally, a surgeon may execute delicate suturing operations with tiny, fine needles to reconnect these or other anatomical bodies. However, installation of sutures with a needle to connect severed tissues can be a difficult and technique-sensitive task. Many factors can make the task difficult, including a very small amount of tissue to work with (e.g., at the urethral stump and at the bladder neck), and proximal sensitive tissues such as ureters at a bladder and a proximal nerve bundle and sphincter at a urethral stump. These factors result in complicated and delicate suturing procedures that, if not performed properly, could result in complications such as leakage, difficulty in healing or failure to heal, or specific conditions such as incontinence or impotence.

To reduce the risks involved in conventional suturing procedures, anastomosis devices have been developed that include a drainage feature and tissue approximating structures that allow for reconnection of tissues without using traditional sutures. Examples of such anastomosis devices are described, for example, in Applicants' co-pending U.S. patent applications having Ser. No. 10/646,383, filed Aug. 21, 2003, entitled "Anastomosis Device and Related Methods"; Ser. No. 10/919,545, filed Aug. 16, 2004, entitled "Anastomosis Device and Related Methods"; and Ser. No. 10/919,775 filed Aug. 16, 2004, entitled "Anastomosis Device and Related Methods", all of which are incorporated herein by reference in their entireties. These anastomosis devices advantageously use tissue approximating structures to reconnect severed tissues during anastomosis procedures, which can both reduce the risks during the surgical procedure and also provide a significant reduction in the amount of time required to perform certain anastomosis procedures.

The tissue approximating structures can be activated by a number of different actuation mechanisms that the surgeon can use to extend and retract the tissue approximating structures relative to adjacent tissue structures, as desired. There is a need, however, to provide an actuation mechanism that is easy for the surgeon to operate, but that can be locked out to prevent or minimize inadvertent movement of the tissue approximating structures.

SUMMARY OF THE INVENTION

Anastomosis devices and related surgical tools and external connecting devices of the invention preferably include an elongated catheter body, tissue approximating structures that can extend from and retract into the elongated body, such as one or multiple sets of tines, and actuating mechanisms for extending and retracting the tissue approximating structures. The anastomosis devices also preferably include a drainage lumen that may extend as a channel through the length of the elongated body and that communicates at its distal end with a drainage aperture, and a balloon at or adjacent to the distal end of the device. The concepts of the invention include devices and methods to create linear movement in order to activate a mechanism from a remote source. That is, the methods and devices of the invention involve activating linear motion in a surgical device, such as an anastomosis device, such that distal internal approximation structures are actuated by a proximal external control mechanism.

More specifically, the tissue approximating structures for the anastomosis devices of the invention preferably include two sets of approximating structures or tines spaced from each other along the length of the catheter body that can be extended and retracted from the catheter body. Each of the sets of tissue approximating structures is preferably sequentially deployable in such a way that the surgeon can activate a first set of tines to engage a first tissue structure, verify that an adjacent second tissue structure is properly positioned relative to the first tissue structure, then activate a second set of tines to engage that adjacent second tissue structure. Each of the sets of tines is preferably controlled by a single actuation mechanism that is attached to the anastomosis device and is positioned outside the patient's body. The actuating mechanisms for the tissue approximating structures are located generally near a proximal end of the device and are preferably connected to the tissue approximating structures with at least one actuation wire. A separate actuation wire is preferably provided for each set of tissue approximating structures to allow for independent extension and retraction of the tissue approximating structures, as desired. In accordance with one embodiment of the invention, both of the actuation wires can be connected within a single actuation mechanism that is manipulated to provide the desired movement of the tissue approximating structures.

The devices of the invention are advantageously provided with a minimal profile to increase patient comfort. In addition, the actuation mechanisms are provided with a relatively smooth exterior surface that does not include sharp edges or surfaces that can snag clothing or injure the patient. The devices are also constructed of materials that are resistant to the surrounding patient environment, and are therefore resistant to rust, chemical reactions, and the like.

BRIEF DESCRIPTION OF THE DRAWINGS

The invention will be further explained with reference to the appended Figures, wherein like structure is referred to by like numerals throughout the several views, and wherein.

DETAILED DESCRIPTION

Figure 7:
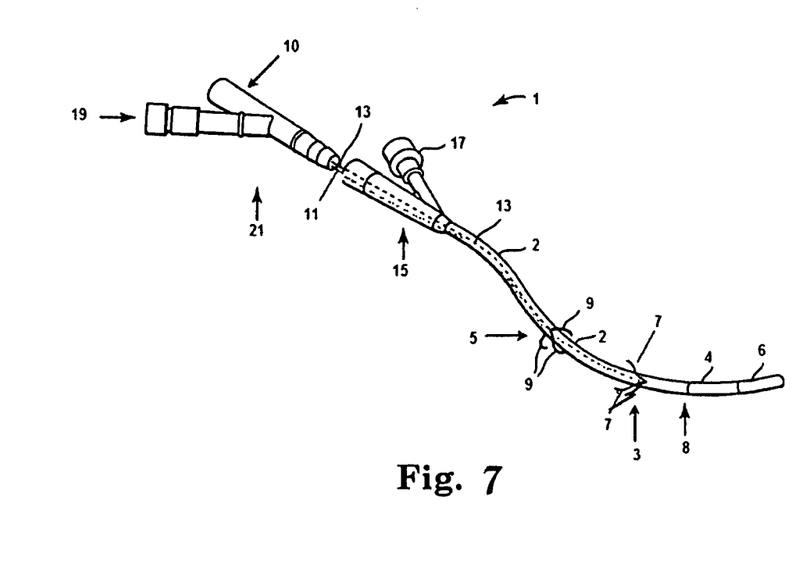
FIG. 7 schematically illustrates an embodiment of an anastomosis device of the present invention.

Please refer to FIG. 7 which shows an example of an anastomosis device of the present invention. Device 1 includes distal end 8, elongate catheter 2, balloon 4, and drainage aperture 6. Two positionable tissue approximating structures are illustrated as components of device 1: proximal tissue approximating structure 5, and distal tissue approximating structure 3, each including a set of tines, 9 and 7, respectively, that extend from and retract into the elongate catheter 2. Device 1 includes proximal end 15 that includes a port 17 that may connect to a lumen (not shown) such as an inflation lumen for balloon 4 or a drainage lumen from aperture 6. Another port 19, of an attachment 21, can also be used with an inflation lumen or a drainage lumen. One or more wires 11 and 13 connect to tissue approximating structures 5, and 3, e.g., as a positioning mechanism, for positioning tines 9 and 7. Actuating mechanisms for each tissue approximating structure are described in detail below with reference to end portion 10.

Figures 1, 6:
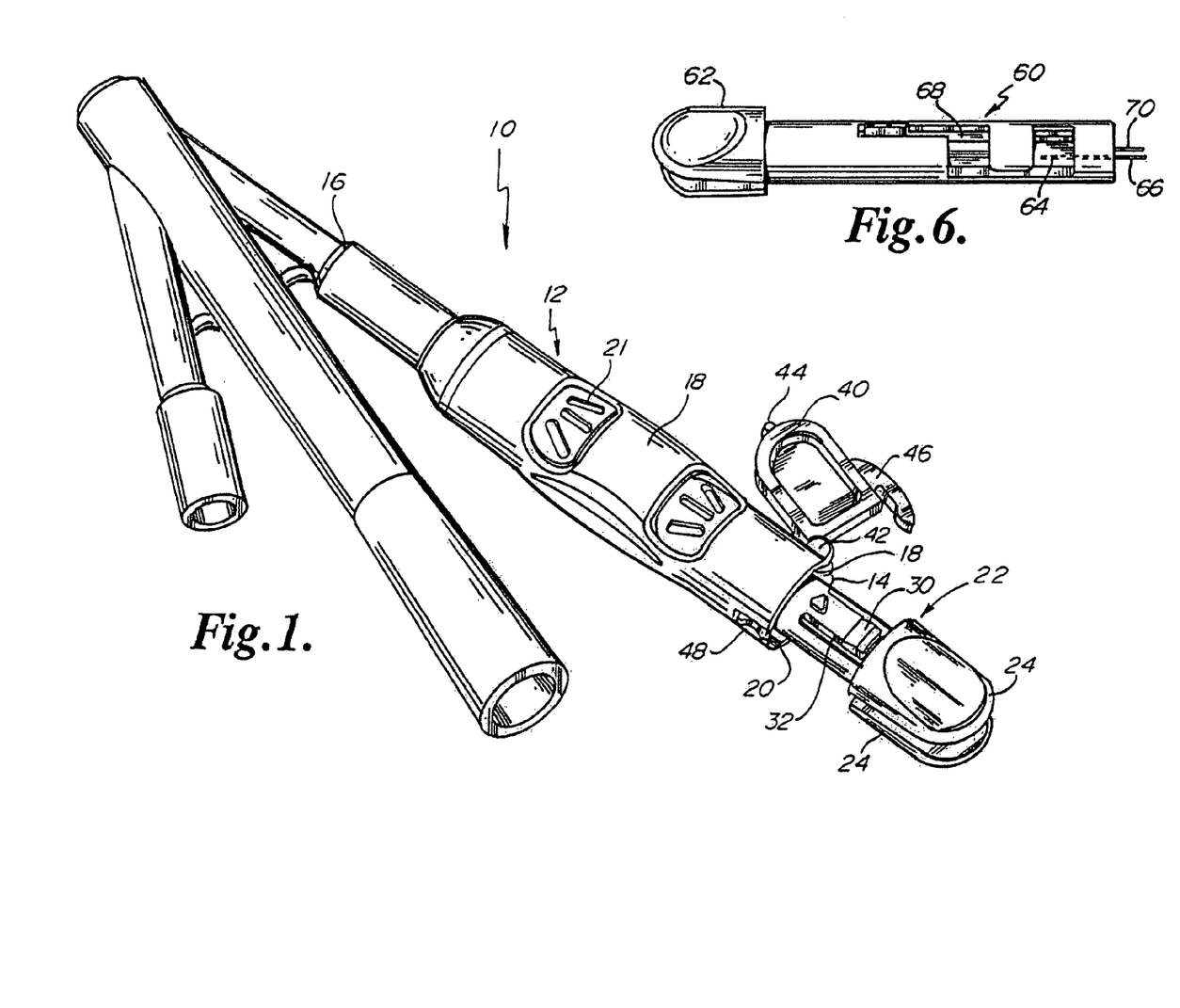
FIG. 1 is a perspective view of an actuation mechanism of an anastomosis device including a lockout tab, where a pair of trigger arms are shown in their intermediate position (e.g., where one of the two sets of tissue approximating structures are deployed)
FIG. 6 is a depiction of the inner workings of an actuation mechanism that utilizes a multi-step sequence for actuating tissue approximating structures.

Referring now to FIGS. 1-6, wherein the components are labeled with like numerals through out the several Figures, and initially to FIG. 1, an end portion 10 of anastomosis device of the type described above is shown. Alternatively, end portion 10 may be used in a different type of device to perform anastomosis or other surgical techniques which required external connection to internal tissues that require deployment of structures such as tines or tissue approximating structure, for example. End portion 10 is generally located at the opposite end of the anastomosis device from the tip portion that is inserted inside the patient and is the portion of the device that will remain outside the patient. End portion includes an actuation mechanism 12 that is used to manipulate the tissue approximation structures, see FIG. 7, when those structures are surgically positioned within a patient's body. In this embodiment, one actuation wire (11 and 13 in FIG. 7) or structure extends through a catheter body from each of the two sets of tissue approximating structures (7 and 9 in FIG. 7), for attachment to and/or communication with actuation mechanism 12.

Actuation mechanism 12 generally includes a body 18 having a proximal end 14 and a distal end 16. Distal end 16 is attached to a shaft or other devices that extend from a catheter body, and proximal end 14 is the free or open end of body 18. Body 18 is a generally tubular body structure having walls 19 surrounding a central elongated opening 20 that is configured for activation and lockout, as described below. Body 18 may further include at least one opening or window 21 that allows viewing into the central opening 20, such as may be useful to determine the position of actuation wires or other components of the device.

Figures 2, 5:
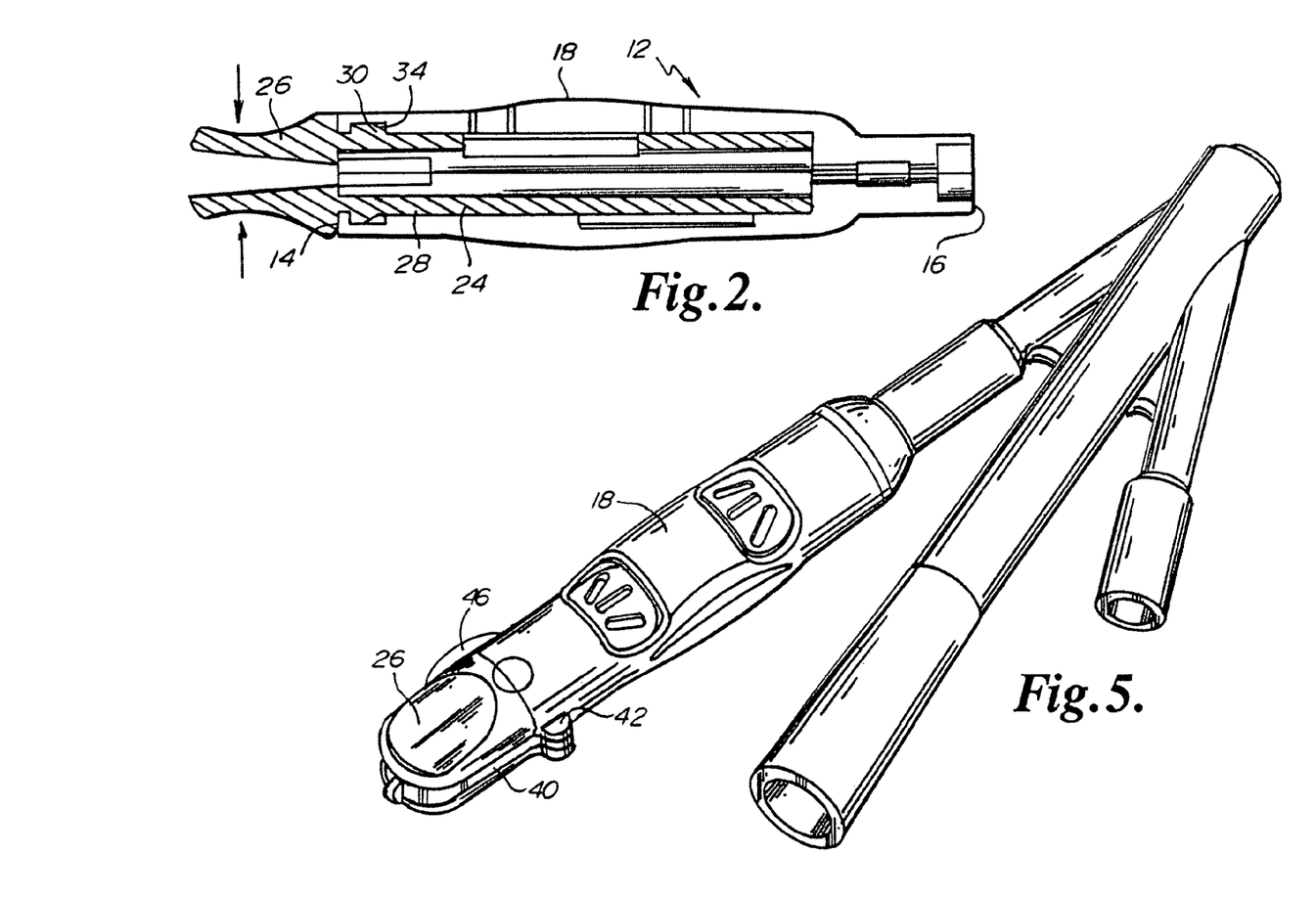
FIG. 2 is a cross-sectional side view of the actuation mechanism of FIG. 1 with the trigger arms in a position that corresponds with the tissue approximating structures being in either their deployed or retracted positions.
FIG. 5 is a perspective view of the actuation mechanism of FIG. 1, with the pair of trigger arms and lockout device shown in their locked position (e.g., where both sets of tissue approximating structures are either deployed or retracted)

Actuation mechanism 12 further includes an actuation insert 22 that is slideable within central opening 20. Actuation insert 22 includes a pair of trigger arms 24 that have a structure that is better shown in the exemplary embodiment of FIGS. 2-4. Referring in particular to FIG. 2, trigger arms 24 each include a flat end portion 26 extending from a curved portion 28. Curved portions 28 are preferably sized, shaped, and spaced relative to each other so that actuation insert 22 can slide relatively easily within central opening 20 of body 18. Each of the curved portions 28 further includes a snap tab 30 that has an elongated notch 32 on both of its sides (see FIG. 1) to allow for flexure of snap tab 30. The walls 19 of body 18 include two recessed areas 34 that are each sized and shaped correspondingly to accept a snap tab 30 when actuation insert 22 is inserted into opening 20.

Figure 3:
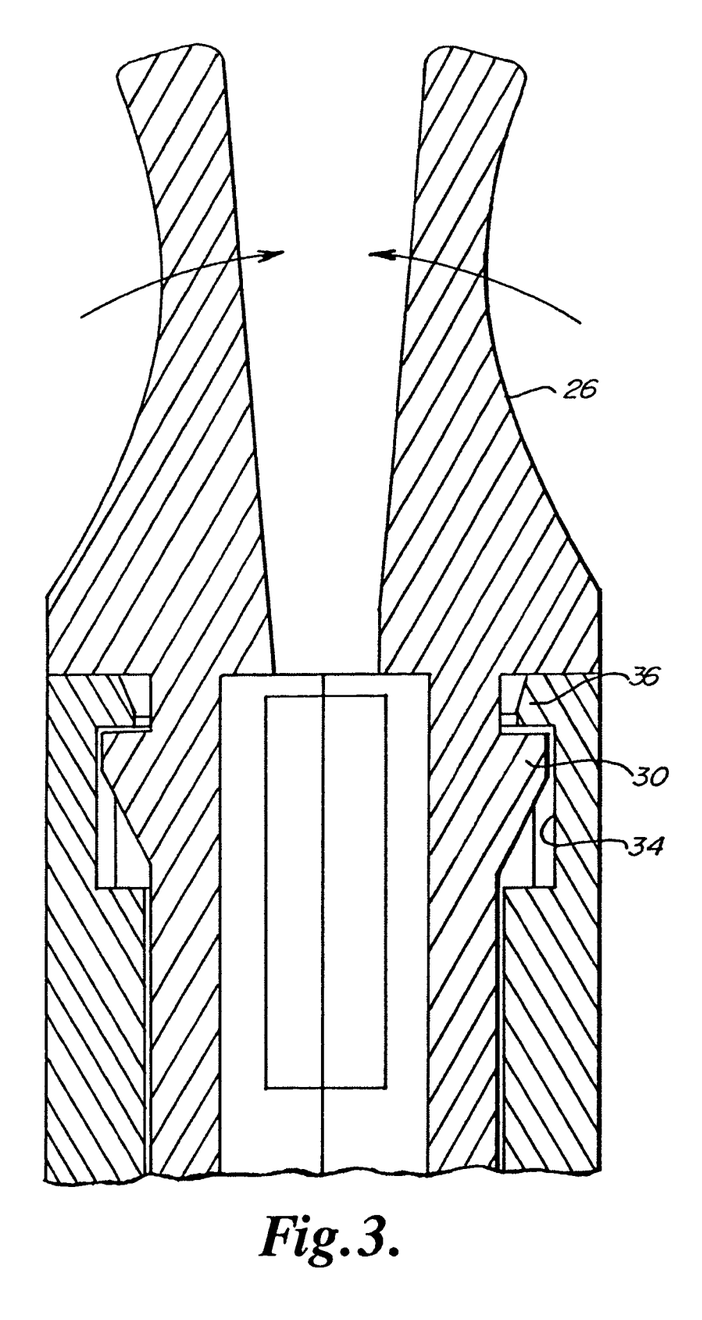
FIG. 3 is an enlarged cross-sectional side view of a portion of the actuation mechanism of FIG. 2 that can be squeezed or compressed to allow manipulation of the actuation wires and connected tissue approximating structures.
Figure 4:
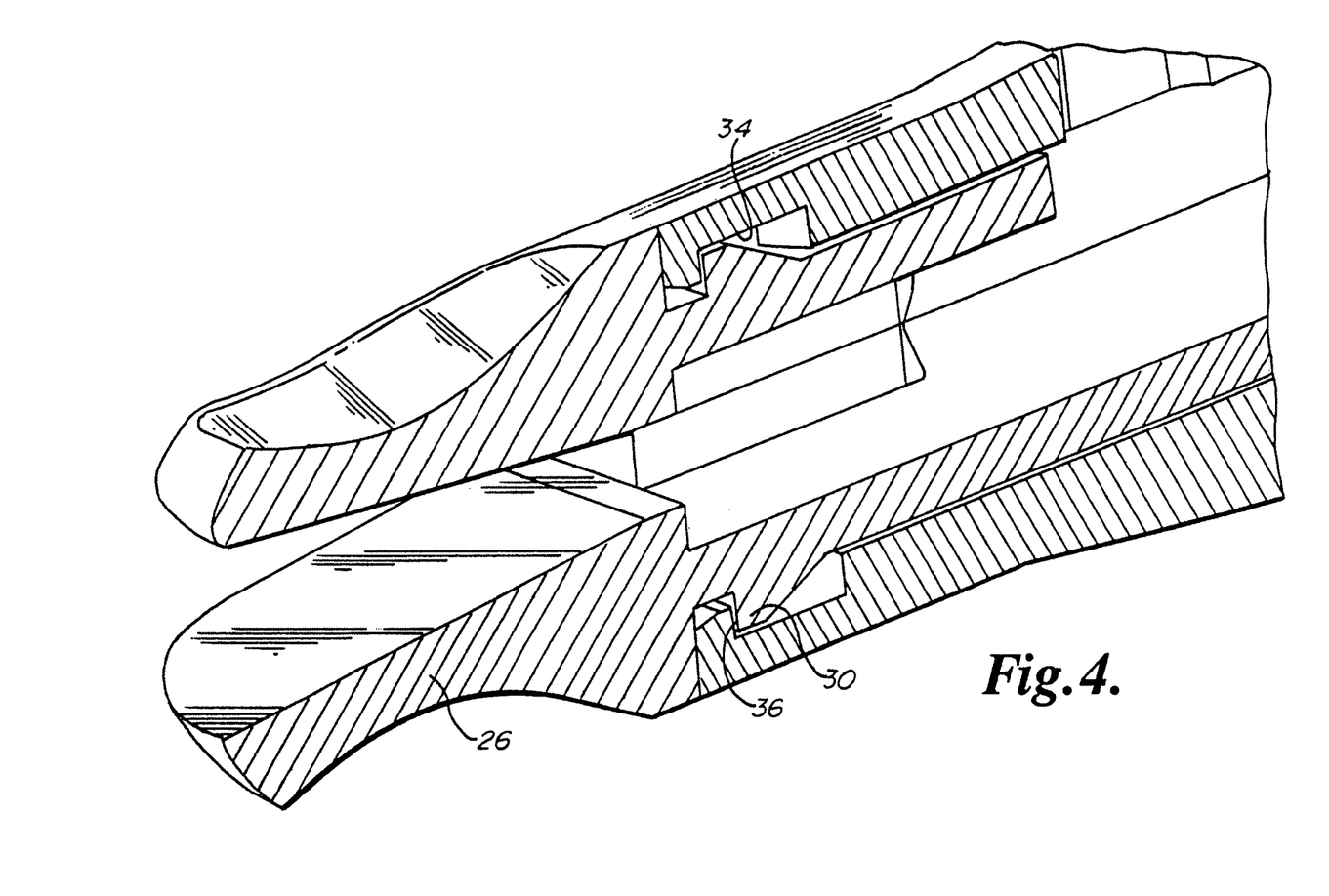
FIG. 4 is a perspective view of the portion of the actuation mechanism illustrated in FIG. 3.

To describe the operation of actuation mechanism 12, actuation insert 22 of FIGS. 2-4 is first assumed to be shown in the configuration in which the tissue approximating structures are in their undeployed or retracted positions within the attached catheter body. It is understood, however, that this configuration of actuation mechanism 12 is similar to the configuration of actuation mechanism 12 when both sets of tissue approximating structures are deployed or extended. Prior to deployment of the tissue approximating structures, snap tabs 30 are positioned within their respective recessed areas 34 to keep actuation insert 22 from moving or sliding along the length of body 18. When it is desired to deploy the tissue approximating structures, flat end portions 26 of trigger arms 24 are squeezed or compressed toward each other until snap tabs 30 can move out of recessed areas 34 and past the stops 36. Actuation insert 22 may then be slid longitudinally outward from central opening 20 of the body 18 until an actuation wire is moved sufficiently to deploy a first set of tissue approximating structures. Body 18 is then rotated 180 degrees, which provides a similar configuration to that shown in FIG. 1, although it is possible that FIG. 1 illustrates the situation immediately before body 18 is rotated. It is possible, however, that the actuation insert 22 is designed so that a rotation of more or less than 180 degrees will provide for different operations of the device. In any case, trigger arms 24 are then again pressed or squeezed toward each other and actuation insert 22 is slid longitudinally back into body 18 until snap tabs 30 are again positioned within recessed areas 34 on the opposite sides of the device from which they were originally positioned. This movement of insert 22 back into body 18 preferably moves an actuation wire until a second set of tissue approximating structures is deployed.

Actuation insert 22 may further include at least one directional arrow 50 to provide a visual reminder to the user of the direction that the insert 22 should be rotated for deployment or retraction of a particular set of tissue approximating structures. The opposite side of actuation insert 22 may also include another arrow (not visible), which also is used to indicate the direction that the insert 22 should be rotated for a different set of tissue approximating structures. Arrow 50 may optionally be color-coded or provided with another type of visual or tactile indicator of the position of a particular set of tissue approximating structures (e.g., to indicate which set of tissue approximating structures is in an active position).

The color or other indicator on the arrow can also be coordinated with a similarly colored band or other indicator that is at or near its respective tissue approximating structure, which may further be coordinated with a colored band or other indicator that can be visible through one of the windows 21. For one example, the device 22 may include a yellow arrow 50, a yellow frame around one of the windows 21, a yellow band at or near one of the sets of tissue approximating structures, and/or another yellow indicator inside the body 18. In this way, the user can determine which set of tissue approximating structures will be activated by moving the actuation insert 22, and can verify that the desired set of tissue approximating structures are deployed by a visual check of the yellow-framed window for a yellow indicator from inside the body 18. Actuation mechanism 12 preferably further includes a lockout device 40 that is shown in FIG. 1 as a relatively flat member that is pivotable about a pivot point 42. Lockout device 40 includes a flat portion 41 having an extending convenience tab 44 and a finger extension 46. When actuation insert 22 is in its inserted position within body 18 as is illustrated in FIG. 5, lockout device 40 can be rotated about pivot point 42 until flat portion 41 is positioned between flat end portions 26 of trigger arms 24. In this position, finger extension 46 will be inserted into an opening 48 of body 18, which may be configured so that finger extension 46 will snap or otherwise positively engage within opening 48 to prevent lockout device 40 from unintentionally moving out of its position between trigger arms 24. The lockout device 40 may also be provided with a feature in place of or in addition to the finger extension 46 that can provide audible or tactile feedback to the user that the device 40 is in its lockout position. As is further shown in FIG. 1, lockout device 40 cannot be rotated to be positioned between trigger arms 24 when insert 22 is in its intermediate position, but can only be used as a lockout device when insert 22 is in its locked position within opening 20 of the body. In this way, the tissue approximating structures are locked out from being either deployed or retracted when in either of these conditions. Further, convenience tab 44 is provided as a small extension from lockout device 40 that extends beyond the sides or ends of flat end portions 26 to allow the user to disengage lockout device 40 to pivot it around its pivot point 42 when it is desired to squeeze trigger arms 24 toward each other.

Although one embodiment of actuation mechanism 12 is described above, it is understood that many variations of the described and illustrated features are considered to be within the scope of the invention. For example, flat end portions 26 are preferably configured to provide an easy grip surface for the user's fingers; however, end portions 26 may be provided with a different size or shape that can more easily accommodate a tool, for example. For another example of a device variation, lockout device 40 may include a different configuration for finger extension 46, or finger extension 46 may be eliminated from the device. For another example, snap tabs 30 may be differently sized, shaped, or configured and/or only one of the trigger arms may include a snap tab 30.

FIG. 6 illustrates another exemplary embodiment of an actuation mechanism 60 that employs a sequence of pulling, then twisting, then pushing of actuation wires to activate tissue approximation structures, such as for bladder and urethral tines. This device includes advancement arms that "pull" an actuation wire to deploy one set of tissue approximating structures, such as bladder tines, then "push" an actuation wire to deploy another set of tissue approximating structures, such as urethral tines. In between the pulling and pushing actions, a rotation of some portion of the actuation mechanisms should desirably occur. The retraction of the tissue approximating structures would then be achieved by performing the opposite actions (i.e, push vs. pull). The tissue approximating structures are deployed or retracted in a predefined sequence (e.g., bladder tines then urethral tines) by a guiding arm 62. The guiding arm 62 engages a first advancement arm 64 and is pulled to advance one actuation wire 66 connected to a first set of tissue approximating structures (e.g., bladder tines). The guiding arm 62 is then twisted and may disengage from the first advancement arm 64, thereby leaving the first advancement arm 64 in a locked position. The guiding arm 62 subsequently or simultaneously engages a second advancement arm 68 which unlocks it, and is then pushed to advance a second actuation wire 70 connected to a second set of tissue approximating structures (e.g., urethral tines). The second advancement arm 68 may then be in a locked position. This predefined sequence could instead be reversed to first push, then twist, then pull the guiding arm, or otherwise altered such that the second set of tissue approximating structures are deployed or retracted before the first set of tissue approximating structures. The various sequences of arm engagements and locking may vary in their order, and it is possible that only one of the advancement arms is lockable. This embodiment of the invention may also include a secondary lockout device or structure that provides a second manner of maintaining the advancement arms and actuation wires in their locked positions.

The various embodiments described herein are not necessarily limited to male-oriented or related surgical procedures and may be applied to either gender and possibly to animals.

The present invention has now been described with reference to several embodiments thereof. The foregoing detailed description and examples have been given for clarity of understanding only. No unnecessary limitations are to be understood therefrom. It will be apparent to those skilled in the art that many changes can be made in the embodiments described without departing from the scope of the invention.

What is claimed:

1. A surgical tool comprising:
an elongated body having a proximal end and a distal end;
at least two sets of tissue approximating structures that are extendible through and retractable back into the elongated body;
a single actuating mechanism at the proximal end of the elongated body for independently extending and retracting each of the at least two sets of tissue approximating structures, wherein the single actuating mechanism comprises a tubular body having an elongated opening at its proximal end, and an actuation insert moveably positioned within the elongated opening, wherein the actuation insert is slideable and rotatable relative to the tubular body; and
wherein the actuation insert of the single actuating mechanism is linearly pushable to activate one of the two sets of tissue approximating structures and linearly pullable to activate the other of the two sets of tissue approximating structures.

2. The surgical tool of claim 1, wherein said single actuating mechanism includes a locking mechanism.

3. The surgical tool of claim 2, wherein the locking mechanism is capable of locking the single actuating mechanism when the at least two sets of tissue approximating structures are both extended or when the at least two sets of tissue approximating structures are both retracted.

4. The surgical tool of claim 1, wherein at least one set of the at least two tissue approximating structures are color-coded and matched to a color-code on the single actuating mechanism.

5. The surgical tool of claim 4, wherein the color-code of the tissue approximating structures and the single actuating mechanism indicate to the user which set of tissue approximating structures will be activated by the push or pull motion of the single actuating mechanism.

6. The surgical tool of claim 1, wherein the actuating mechanism further incorporates a rotating motion between the pushing motion and the pulling motion.

7. The surgical tool of claim 1, wherein the actuation insert is longitudinally slideable relative to the tubular body in a first direction to deploy a first of the two sets of tissue approximating structures and is longitudinally slideable relative to the tubular body in a second direction to deploy a second of the two sets of tissue approximating structures.

8. The surgical tool of claim 7, wherein the actuation insert is rotatable relative to the tubular body after longitudinally sliding it in the first direction to disengage the first set of tissue approximating structures and engage the second set of tissue approximating structures.

9. An anastomosis device comprising:
an elongated body having a proximal end and a distal end;
a first and a second set of tissue approximating structures that are extendible through and retractable back into the elongated body; and
a single actuating mechanism at the proximal end of the elongated body for independently extending and retracting the first and second sets of tissue approximating structures, wherein the single actuating mechanism comprises a guiding arm, a first advancement arm operatively engageable with the guiding arm, and a second advancement arm operatively engageable with the guiding arm;
wherein the first set of tissue approximating structures is actuatable when the guiding arm is engaged with the first advancement arm, and wherein the second set of tissue approximating structures is actuatable when the guiding arm is engaged with the second advancement arm.

10. The anastomosis device of claim 9, wherein engagement of the guiding arm with the first advancement arm allows for the guiding arm to be pulled linearly to actuate the first set of tissue approximating structures, wherein the guiding arm is rotated to disengage the first advancement arm from the guiding arm and engage the second advancement arm, and wherein the guiding arm is then linearly pushed to actuate the second set of tissue approximating structures.

11. The anastomosis device of claim 10, wherein disengaging the guiding arm from the first advancement arm operates to lock the position of the first advancement arm.

12. The anastomosis device of claim 9, wherein the first set of tissue approximating structures comprises a set of bladder tines and wherein the second set of tissue approximating structures comprises a set of urethral tines.

13. The anastomosis device of claim 9, further comprising a first actuation wire attached to the first set of tissue approximating structures and a second actuation wire attached to the second set of tissue approximating structures.

* * * * *